United States Patent [19]

Wolfe et al.

[11] Patent Number: 4,510,246

[45] Date of Patent: Apr. 9, 1985

[54] ISOLATION OF CYCLASE, EPIMERASE AND A RING EXPANSION ENZYME FOR PRODUCING UNNATURAL CEPHALOSPORINS

[75] Inventors: Saul Wolfe, Kingston; Donald Westlake; Susan Jensen, both of Edmonton, all of Canada

[73] Assignee: Queen's University at Kingston, Kingston, Canada

[21] Appl. No.: 410,302

[22] Filed: Aug. 23, 1982

[51] Int. Cl.³ .......................... C12N 9/00; C12N 9/06; C12P 35/00; C12P 35/06
[52] U.S. Cl. ...................................... 435/183; 435/43; 435/47; 435/49; 435/190; 435/191; 435/814; 435/815; 435/816
[58] Field of Search ...................... 435/43, 47, 49, 183, 435/190, 191, 814, 815, 816, 926

[56] References Cited

U.S. PATENT DOCUMENTS

| | | | |
|---|---|---|---|
| 4,075,061 | 2/1978 | Fleming et al. | 435/47 |
| 4,178,210 | 12/1979 | Demain et al. | 435/47 |
| 4,248,966 | 2/1981 | Demain et al. | 435/43 |
| 4,307,192 | 12/1981 | Demain et al. | 435/47 |

Primary Examiner—David M. Naff
Attorney, Agent, or Firm—Richard J. Hicks

[57] ABSTRACT

The enzymes, cyclase, epimerase and a ring expansion enzyme, are isolated separately from a cell-free extract of a prokaryotic beta-lactam producing organism. The isolated enzymes are used to produce unnatural cephalosporins from polypeptide precursors. Isolation is carried out by adding ammonium sulfate to 40% saturation to the cell-free extract to precipitate contaminating proteins, adding ammonium sulfate to 70% saturation to the resultant supernatant to precipitate the enzymes, suspending the precipitated enzymes in a buffer, separating epimerase from the suspension by gel filtration, and separating cyclase and the ring expansion enzyme from each other by ion exchange chromatography.

3 Claims, No Drawings

ISOLATION OF CYCLASE, EPIMERASE AND A RING EXPANSION ENZYME FOR PRODUCING UNNATURAL CEPHALOSPORINS

BACKGROUND OF THE INVENTION

1. Field of the Invention

This invention relates to a cell-free process for producing cephalosporin antibiotics from polypeptides and derivatives thereof.

2. The Prior Art

The beta-lactam family of natural products includes the penicillins:

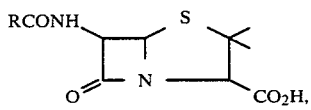

cephalosporins:

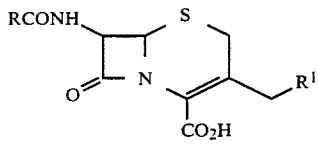

and cephamycins

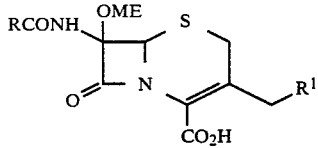

in which the beta-lactam ring is fused to a five or six membered sulfur containing ring; together with clavulanic acid

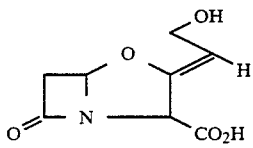

in which the beta-lactam is fused to a five membered oxygen containing ring;
the carbapenems

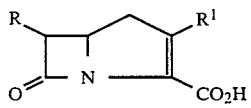

in which the beta-lactam is fused to a five membered carbon containing ring;
and the nocardins and monobactams

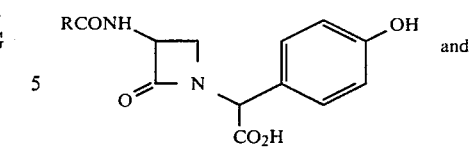

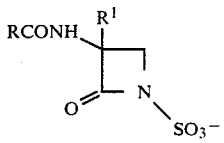

which are monocyclic compounds.

Although there are many members of this family, only two can be used directly in medicine without structural change. These are penicillin G, the penicillin in which R=benzyl, and clavulanic acid. All other clinically important beta-lactam compounds have been prepared from one or other of the natural products by structural change. For many years the changes have been generally effected by substitution around the peripheries of the various ring systems and not in the ring systems themselves. Since 1974, however, efforts have been concentrated on nuclear modification of the beta-lactam natural product to produce cephalosporins, oxacephems and their derivatives. Such efforts have generally resulted in complex chemical processes containing upwards of 16 steps with the result that the products are obtained in generally low yield and at extremely high cost. Moxalactam ®, for example, a third generation cephalosporin, is approximately five times more expensive than cephalothin, a first generation cephalosporin; and cephalothin is, in turn, approximately fifty times more expensive than ampicillin, a semi-synthetic penicillin (Drug Topics Red Book 1981).

Attention has therefore turned to alternative methods of synthesis, and in particular to microbiological methods. Cell-free syntheses of penicillins and the related cephalosporins are known in the art and attention is directed to U.S. Pat. No. 4,178,210 issued Dec. 11, 1979 to A. L. Demain et al, which teaches conversion only of the D-form, penicillin N, to a cephalosporin compound. In U.S. Pat. No. 4,248,966 issued Feb. 3, 1981, A. L. Demain et al teach the production of isopenicillin derivatives, in a cell-free system using an extract from *Cephalosporium acremonium,* from a tripeptide composed of unsubstituted or β substituted D-valine, unsubstituted or substituted L-cysteine, and L-α-aminoadipic acid or its analogs. Freezing of the cell-free extract resulted in inactivation of certain enzymes so that conversion did not proceed past the isopenicillin stage. In U.S. Pat. No. 4,307,192 issued Dec. 22, 1981, A. L. Demain et al teach the use of a fresh (i.e. not frozen) cell-free extract of *C. acremonium* so as to preserve the racemase (epimerase) agent or agents necessary for the converstion of isopenicillin N to penicillin N, a necessary intermediate step in the process for conversion of L-aminoadipyl-L-cysteinyl-D-valine (abbreviated to LLD in the reference but hereinafter ACV) via an oxidative cyclization step to isopenicillin N, epimerization to penicillin N and oxidative ring expansion to desacetoxycephalosporin C.

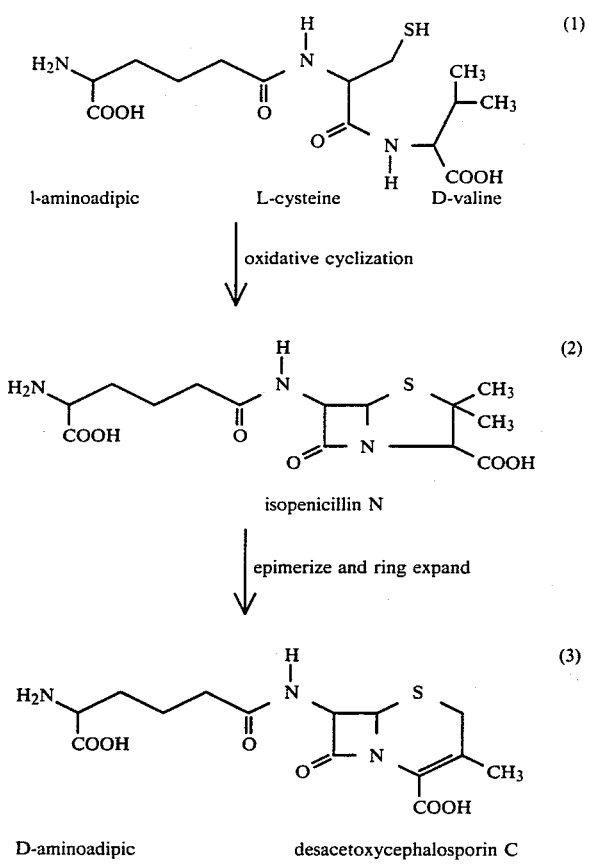

l-aminoadipic  L-cysteine  D-valine isopenicillin N

D-aminoadipic  desacetoxycephalosporin C

The activity of the racemase agent in a cell-free extract of *C. acremonium* was first recognized by Konomi et al, Biochem. J. Vol. 184, p 427–430, 1979, and confirmed by Baldwin et al, Biochem J. Vol. 194, 649–651, 1981, and Jayatilake et al, Biochem. J. Vol. 194, 649–647, 1981 who also recognized the extreme lability of the racemase agent so that recovery of the racemase agent per se is believed to be impossible. The lability of the racemase agent is believed to preclude use of cell-free extracts of *C. acremonium* for high yield commercial production of cephalosporins.

It is, therefore, an object of the present invention to provide an integrated cell-free process for producing a cephalosporin compound from a peptide of the general formula

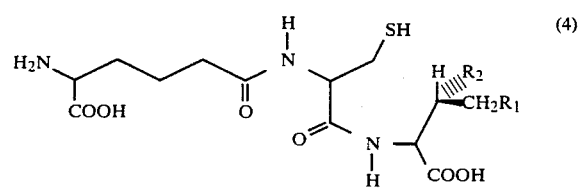

where $R_1$ is hydrogen, a lower alkyl or functionalized carboxylic group, and $R_2$ is hydrogen or a lower alkyl group, using stable cell-free extracts from prokaryotic organisms.

These and other objects of the invention will be apparent from the following description of the preferred embodiments.

SUMMARY OF THE INVENTION

It has now been discovered that certain cell-free extracts of prokaryotic organisms such as *Streptomyces clavuligerus*, *Streptomyces cattleya* and *Streptomyces lipmanii*, can be separated into three fractions by a three stage treatment to provide three stable and separate enzymes: (a) epimerase (MW approx. 60,000) which may be used, for example, to epimerize isopenicillin N to penicillin N; (b) cyclase (MW approx. 36,500) which may be used, for example, to cyclize ACV to isopenicillin N; and (c) ring expansion enzyme (MW approx. 29,000) which may be used, for example, to ring expand penicillin N to deacetoxycephalosporin C.

Thus, by one aspect of this invention there is provided a process for producing unnatural cephalosporins of the formula

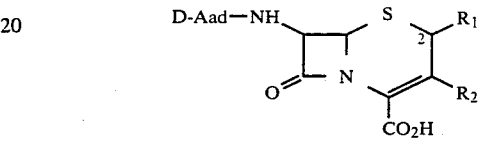

where $R_1 =$ H, lower alkyl, or functionalized carboxylic and $R_2 =$ H or lower alkyl and derivatives thereof, comprising reacting a starting material comprising L-α-aminoadipyl-L-cysteinyl-D-valine and analogs thereof in which an amino acid is substituted for the valine moiety, with cyclase, epimerase and a ring expansion enzyme isolated from a cell-free extract of a prokaryotic organism for sufficient time and in the presence of sufficient co-factors to produce said cephalosporins.

By another aspect of this invention there is provided a process for isolating cyclase, epimerase and a ring expansion enzyme from a cell-free extract of a prokaryotic organism comprising:

(a) precipitating contaminating proteins from said cell-free extract by addition of ammonium sulfate to 40% saturation;

(b) separating precipitated protein from a supernatant;

(c) adding further ammonium sulfate to 70% saturation to said supernatant thereby precipitating desired said enzymes;

(d) suspending said precipitated enzymes in pH 7 buffer; and (e) chromatographically separating the desired enzymes from each other.

DESCRIPTION OF THE PREFERRED EMBODIMENTS

In the following description, reference will be made particularly to the conversion of ACV (1) to deacetoxycephalosporin which is useful as an antibiotic as such or as a starting compound for the production of cephalosporin antibiotics such as Cephalexin ®. It will be appreciated, however, that the biochemical techniques of the present invention are equally applicable to other starting materials and it is within the purview of the present invention to substitute the valine moiety in the preferred ACV starting material with any of the readily available amino acids for conversion to the analogous cephalosporins which are useful as antibiotics, or as starting materials for antibiotics such as Cefoxitin ® or Ceftizoxime ®. Thus, the starting material may be regarded as having the general formula (4)

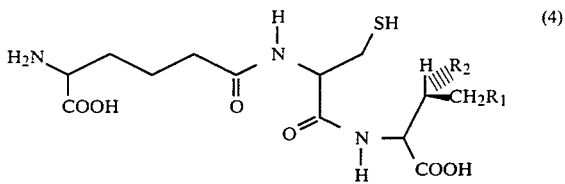

(4)

where $R_1$ and $R_2$ are as hereinbefore described. The amino acids which may be used thus include:

| $R_1$ | $R_2$ | Compound |
|---|---|---|
| H | $CH_3$ | Valine |
| H | H | α-aminobutyric acid |
| H | $C_2H_5$ | allo isoleucine |
| $CH_3$ | $CH_3$ | isoleucine |
| COOH | H | glutamic acid |
| $CH_2NH-\underset{\underset{NH}{\|}}{\overset{\|}{C}}NH_2$ | H | arginine |
| $CONH_2$ | H | glutamine |
| $CH_2CH_2NH_2$ | H | lysine |

The naturally-occurring beta-lactam compounds are formed as secondary metabolites of both eukaryotic and prokaryotic organisms. Simply stated, a eukaryote is a higher life form, and it has a more complicated cell structure, which restricts the types of compounds that can be synthesized or metabolized. Examples of eukaryotic beta-lactam-producing organisms are the fungi *Penicillium chrysogenum* and *Cephalosporium acremonium*. A prokaryote, on the other hand, is a lower, earlier, life form, with a more primitive cell structure, which allows a greater variety of chemical transformations to take place. This suggests, again simply, that prokaryotes are more versatile at organic synthesis than are eukaryotes, provided that this versatility can be understood and controlled. Examples of prokaroytic beta-lactam-producing organisms are the actinomycetes *Streptomyces clavuligerus, S. cattleya* and *S. lipmanii.*

As an illustration of the differing capabilities of eukaryotic and prokaryotic beta-lactam-producing organisms, *P. chrysogenum*, a eukaryote, synthesizes ACV and converts this peptide sequentially to penicillin as the only stable beta-lactam-containing end product. *C. acremonium*, also a eukaryote, synthesizes the same tripeptide and converts this peptide sequentially to penicillin and cephalosporin. In contrast, the prokaryote *S. clavuligerus* synthesizes penicillin, cephalosporin and cephamycin from one amino acid-containing precursor and, *at the same time,* clavulanic acid, from a completely different precursor. The prokaryote *S. cattleya* synthesizes penicillin and cephalosporin from one precursor and, at the same time, the carbapenem thienamycin, from a different precursor.

*S. clavuligerus*, for example, is a well known microorganism and several strains are available, on an unrestricted basis, from the Northern Regional Research Laboratory, Peoria, Ill., U.S.A. under the name NRRL 3585, among others. Other prokaryotic organisms, as described above, are equally freely available. The NRRL 3585 organism must be cultured in a medium and under conditions conducive to the production of β-lactam compounds, as described in more detail hereinafter.

There are several methods for cell breakage prior to obtaining a cell-free extract, including French pressure cell, Omnimixer-plastic beads and the preferred sonication. The preferred treatment comprises sonication for 30 seconds on 48 hour washed cells, followed by centrifugation. The supernatant from this treatment is designated "crude cell-free extract". The crude extract may be separated into three enzyme fractions in a three stage treatment. In the first stage, contaminating proteins are precipitated by addition of ammonium sulfate to 40% saturation, and separated from the supernatant by centrifugation or other conventional means. Addition of more ammonium sulfate to 70% saturation precipitates the desired enzyme activities. The resulting pellet, suspended in pH 7 buffer is termed "salt-precipitated cell-free extract" (SPCFX). This SPCFX retains all the desired enzyme activities, and shows reduced baseline contamination in HPLC assays. In the second stage, the epimerase (isopenicillin N→penicillin N) (MW 60,000) is cleanly separated from the cyclase (ACV→isopenicillin N) (MW 36500) and ring expansion (penicillin N→desacetoxycephalosporin C) (MW 20,000) enzymes, by gel filtration chromatography of the SPCFX on, for example, Sephadex ®G-200 (Pharmacia, Sweden). In the third stage, the cyclase and ring expansion enzymes are separated by ion exchange chromatography on, for example, DEAE Trisacryl resin (sold by L.K.B., Sweden). A 100-fold purification of the cyclase is achieved in this manner. Thus, for the first time three distinct enzyme reagents each having a different enzymatic activity and physical characteristics (e.g., different molecular weights) and which are stable over an extended period of time (of the order of months) under suitable storage conditions of temperature and pH (preferably about −20° C. and pH7) have been prepared. The enzymes may be stored and used quite separately or may be stored and used as a mixture as required.

Analogous treatment using SPCFX from *C. acremonium* yields the cyclase and ring expansion enzymes only. As noted above the epimerase is entirely absent due to its extreme lability.

Following preparation of the three enzymes, ACV dimer or an analog thereof as described above, may be reacted therewith under aerobic conditions, in the presence of the required co-factors such as ferrous ions usually in the form of ferrous sulfate, an antioxidant such as ascorbic acid, a reducing agent such as dithiothreitol (DTT) and a co-substrate such as α-ketoglutarate, for sufficient time at about 20° C. and at a suitable pH of about 7 to produce desacetoxycephalosporin C or an analog thereof.

EXAMPLE 1

Production of SPCFX (a) Culture of *S. clavuligerus*

*Streptomyces clavuligerus* NRRL 3585 was maintained on a sporulation medium composed of tomato paste, 20 g; oatmeal, 20 g; agar, 25 g, in 1 liter of distilled water, pH 6.5.

Inoculated plates were incubated 7–10 days at 28° C. Spores were scraped off into sterile distilled water (5 ml/plate) and used to inoculate, 2% v/v, 25 ml/125 ml flask, seed medium of the following composition: glycerol, 10 ml; sucrose, 20 g; soy flour, 15 g; yeast extract, 1 g; tryptone, 5 g; $K_2HPO_4$, 0.2 g in 1 liter of distilled water, pH 6.5. Inoculated seed medium was incubated for 3 days and used to inoculate, 2% v/v, 100 ml amounts of production medium in 500 ml flasks. Production medium consisted of soluble starch, 10 g; L asparagine, 2 g; 3-N-morpholinopropane-sulfonic acid, 21 g; $MgSO_4.7H_2O$, 0.6 g; $K_2HPO_4$, 4.4 g; $FeSO_4.7H_2O$, 1 mg; $MnCl_2.4H_2O$, 1 mg; $ZnSO_4.7H_2O$, 1 mg; and $CaCl_2.2H_2O$, 1.3 mg in 1 liter of $H_2O$, pH 6.8. Inoculated production medium was incubated 40–48 h and the cells were then collected by filtration and used to prepare cell-free extracts. All incubations were at 27° C. on a gyrotory shaker (250 rpm, 19 mm eccentricity).

(b) Preparation of Cell-Free Extracts

Cell-free extracts were prepared by washing 40–48 h cells of *S. clavuligerus* in 0.05M Tris-HCl buffer, pH b 7.0+0.1 mM dithiothreitol (DTT) (100 ml/100 ml culture). Washed cells were resuspended to 1/10 of the original culture volume in the same buffer and disrupted by sonication in an ice water bath for 2×15 sec at maximum intensity (300 watts, Biosonik III, Bronwill Scientific). Broken cell suspensions were centrifuged 1 h at 100,000 xg. All cell-free extracts were stored frozen at −20° C.

Salt-precipitated cell-free extract was prepared by gradual addition of streptomycin sulfate to cell-free extract with gentle stirring at 4° C. to a final concentration of 1%, w/v. After 15 min at 4° C., precipitated nucleic acid was removed by centrifugation for 15 min at 15,000 xg. Solid ammonium sulfate was then gradually added to the supernatant with gentle stirring at 4° C. until 40% saturation was reached. After 15 min at 4° C. the suspension was centrifuged as above and the pellet discarded. Additional ammonium sulfate was then added to the supernatant, as above, until 70% saturation was reached. Following centrifugation, the pellet was resuspended to its original volume in 0.05M Tris-HCl buffer pH 7.0 containing 0.1 mM DTT. The enzyme solution was then concentrated to 1/10 of the original volume by ultrafiltration with an Amicon ®PM-10 filter.

Cyclization Assay System

Cyclization activity of enzyme preparations was measured in reaction mixtures containing: bis-δ-(L-α-aminoadipyl-L-cysteinyl-D-valine) $(ACV)_2$ 0.306 l mM, DDT 4 mM, Na ascorbate 2.8 mM, $FeSO_4$ 45 μM, tris-HCl buffer 0.05M, pH 7.0, enzyme preparation 0.03–0.3 ml, final volume 0.4 ml. Reaction mixtures were incubated at 20° C. for up to 4 hours and stopped by cooling on ice or by the addition of 0.4 ml methanol.

Ring Expansion Assay System

Ring expansion activity was followed using the cyclization assay system described above but supplemented with ATP 0.5 mM, α-ketoglutarate 1 mM, KCl 7.5 mM, and $MgSO_4$ 7.5 mM. Total volume and incubation conditions were the same as for the cyclization assay.

EXAMPLE 2

Separation of Enzyme Fractions (a) Separation of Epimerase by Gel Filtration Chromatography of SPCFX 2.5 ml of SPCFX was applied to a Sephadex ®G-200 superfine column (2.5 cm×40 cm) which had been equilibrated in 0.05M Tris-HCl buffer pH 7.0 containing 0.1 mM DTT. The column was eluted with the same buffer and 2.5 ml fractions were collected. Fractions were monitored for protein by measuring UV absorption at 280 nm, and were assayed for cyclase, epimerase and ring expansion activities as described previously.

Active fractions were pooled and concentrated by ultrafiltration using an Amicon ®PM-10 filter.

(b) Separation of Cyclase and Ring Expansion Enzyme by Ion Exchange Chromatography of SPCFX 2.5 ml of SPCFX was applied to a DEAE-Trisacryl ® column (1.6×25 cm) which had been equilibrated in 0.1M Tris-HCl buffer pH 7.0 containing 0.1 mM DTT. The column was washed with 50 ml of the above buffer and then eluted with a linear gradient of 150 ml each of initial starting buffer vs 0.4M Tris-HCl buffer pH 7.0 containing 0.1 mM DTT. 2.5 ml fractions were collected and monitored for protein content by measuring UV-absorption at 280 nm. Fractions were also monitored for conductivity and were assayed for cyclization, epimerase and ring expansion activity as described previously. Active fractions were pooled and concentrated and desalted by ultrafiltration using an Amicon ®PM-10 filter.

Both separations were performed at 4° C., and the enzyme products were stored at −20° C. or lower as they were found to lose activity overnight at room temperature.

EXAMPLE 3

Preparation of ACV and Related Compounds

N-BoC-S-trityl-L-cysteine was coupled with the benzhydryl ester of D-valine to give a fully protected dipeptide 5.

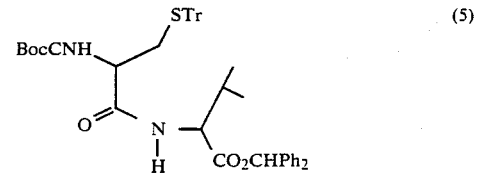

A 15 minute treatment with anhydrous formic acid at room temperature led to crystalline, partially protected peptide 6.

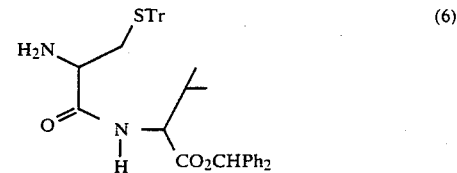

Conversion to fully protected ACV (7)

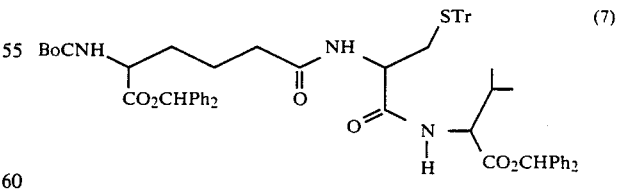

was achieved by coupling peptide (6) with (8)

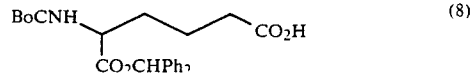

Deprotection of (7) was achieved in two stages:

(a) removal of the trityl group, with iodine in methanol;

(b) removal of all other protecting groups by overnight treatment with formic acid, leading to ACV disulfide (9). The ACV is best stored in this form and may be readily converted to ACV (1), as needed, with dithiothreitol. This synthesis is readily adaptable to systematic modification of the aminoadipyl moiety and compounds such as N-acetyl-ACV and its cyclic analog N-acetyl isopenicillin N, may be similarly prepared from N-acetyl-L-α-aminoadipic acid alpha-benzhydryl ester as the starting material.

EXAMPLE 4

Preparation of
δ-(L-α-aminoadipyl)-L-cysteinyl-D-alloisoleucine
(ACI)

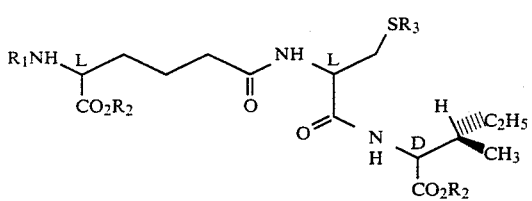

This compound was prepared from L-α-aminoadipic acid, L-cysteine and D-alloisoleucine, as described for the synthesis of the natural cephalosporin precursor δ-(L-α-aminoadipyl)-L-cysteinyl-D-valine by S. Wolfe and M. G. Jokinen, Canadian Journal of Chemistry, Volume 57, pages 1388–1396, 1979. This led, successively, to the fully protected tripeptide ($R_1$=t-butoxycarbonyl, $R_2$=benzhydryl, $R_3$=trityl), m.p. 91°–93° (ethyl acetate-petroleum ether), $R_f$ 0.54 (methylene chloride-ethyl acetate, 9:1; yellow with palladium chloride), the detritylated compound ($R_1$=t-butoxycarbonyl, $R_2$=benzhydryl, $R_3$=disulfide), m.p. 114°–116° (methanol), $R_f$ 0.76 (methylene chloride-ethyl acetate, 4:1, yellow with palladium chloride), and the completely deprotected compound ($R_1$=$R_2$=H, $R_3$=disulfide), $R_f$=0.22 (methyl ethyl ketone-water-acetic acid, 4:1:1, purple with ninhydrin), $^1$Hmr (D$_2$O) δ: 0.90 (3H, d, 6 Hz), 0.91 (3H, 5, 7 Hz), 1.30 (2H, m), 1.73 (2H, br t), 1.88 (2H, br t), 2.01 (1H, m), 2.39 (2H, br t), 3.00 (1H, q, 8, 15 Hz), 3.16 (1H, q, 5, 15 Hz), 3.76 (1H, t, 6 Hz), 4.40 (1H, d, 4 Hz), 4.73 (1H, br s). The latter compound is converted into the active form ($R_1$=$R_2$=$R_3$=H) upon treatment with dithiothreitol.

EXAMPLE 5

Preparation of
δ-(L-α-aminoadipyl)-L-cysteinyl-D-α-aminobutyrate
(ACAb)

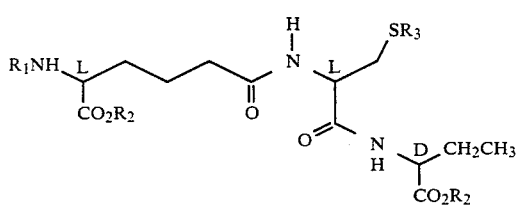

This compound was prepared, as in Example 4, via the intermediates $R_1$=t-butoxycarbonyl, $R_2$=benzyhydryl, $R_3$=trityl: $R_f$ 0.63 (toluene-ethyl acetate, 2:1); $R_1$=t-butoxycarbonyl, $R_2$=benzhydryl, $R_3$=disulfide: $R_f$ 0.48 (toluene-ethyl acetate, 2:1); and $R_1$=$R_2$=H; $R_3$=disulfide: $R_f$=0.1 (methyl ethyl ketone-water-acetic acid, 4:1:1), $^1$Hmr (D$_2$O) δ: 0.91 (3H, t, 7.5 Hz), 1.59–2.00 (6H, m), 2.41 (2H, t, 7 Hz), 3.97 (1H, q, 8.5, 14 Hz), 3.21 (1H, q, 5, 14 Hz), 3.75 (1H, t, 7 Hz), 4.18 (1H, q, 5, 8.5 Hz), 4.73 (1H, m). This last compound is converted into the active form ($R_1$=$R_2$=$R_3$=H) upon treatment with dithiothreitol.

EXAMPLE 6

Cyclization of ACV

To 0.4 ml of reaction mixture were added 0.9 mM of ACV dimer as produced in Example 3, 50.0 mM Tris-HCl pH 7.0 buffer and a mixture of the three enzymes as produced in Example 1 from a cell-free extract of *S. clavuligerus*, together with 45.0 μM ferrous sulfate and 2.8 mM ascorbic acid as optimized amounts of essential co-factors. DTT was added in excess of the amount required to reduce ACV dimer to ACV monomer. The reaction was continued for approximately 2 hours at 20° C. and then terminated by addition of 0.4 ml methanol to precipitate protein. It was found, by bioassay and HPLC procedures (described in more detail hereinafter) that the peptide had been converted to a mixture of isopenicillin N and penicillin N. Ring expansion to a cephalosporin did not occur. The experiment was repeated with the addition of 1 mM of a standard oxygenase type enzyme co-factor, alpha-ketoglutarate, and in this case it was found that the ACV was converted to desacetoxycephalosporin C.

EXAMPLE 7

The procedures of Example 6 were repeated using L-aspartyl, L-glutamyl, D-α-aminoadipyl, adipyl, glycyl-L-α-aminoadipyl and N-acetyl-L-α-aminoadipyl-containing peptides. It was found that the L-aspartyl, L-glutamyl and D-α-aminoadipyl containing peptides did not cyclize. Cyclization was observed with adipyl, glycyl-L-α-aminoadipyl and N-acetyl-L-α-aminoadipyl containing peptides. The adipyl compound gave ca 20% cyclization to the corresponding penicillin, carboxybutylpenicillin but SPCFX converted the glycyl and N-acetyl compounds to penicillin N and isopenicillin N, via an initial deacylation of these peptides to ACV. Purified cyclase from *S. clavuligerus* did not cyclize the glycyl-L-α-aminoadipyl containing peptide. These results suggest that the enzymatic conversion of an ACV analog to an unnatural cephalosporin nucleus requires (i) a δ-L-α-aminoadipyl side chain and (ii) an enzyme system containing the epimerase. A prokaryotic system is, therefore, required. Modification of the valinyl moiety, as noted above, has been considered in detail. Substrates modified in the valinyl moiety such as:

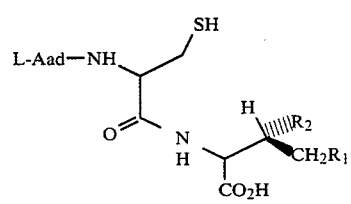

where $R_1$ is H, a lower alkyl or functionalized carboxylic group; and $R_2$ is H or a lower alkyl group may be cyclized with carbon-sulfur bond formation with retention of configuration at the beta carbon of the valine analog, leading to isopenicillin N analogs of the type:

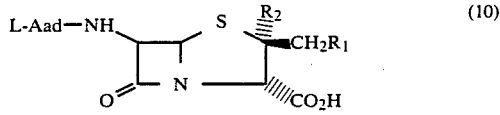

Following epimerization to penicillin N analogs of the type:

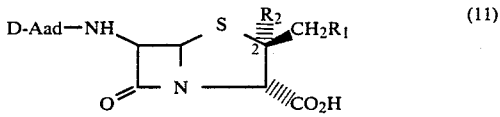

ring expansion leads to cephalosporin analogs of the type:

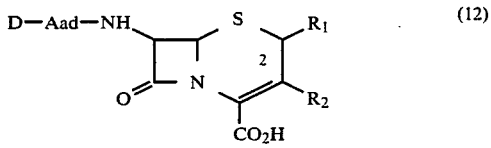

with transfer of the beta carbon atom attached to $C_2$ of (11) into $C_2$ of the six membered ring.

EXAMPLE 8

Bioassay of Beta-lactam Compounds

Antibiotic in reaction mixtures was estimated by the agar diffusion method. Cyclization reaction mixtures were bioassayed using *Micrococcus luteus* ATCC 9341 and *Escherichia coli* Ess as indicator organisms. Ring expansion reaction mixtures were bioassayed using *E. coli* Ess as indicator organism in agar plates supplemented with penicillinase at $2 \times 10^5$ units/ml.

High Performance Liquid Chromatography (HPLC)

Methanol inactivated reaction mixtures were centrifuged at 12,000 xg for 5 min to remove precipitated protein before analysis. The chromatographic equipment used was: M-6000A pump, UK-6 injector, M-480 variable wavelength detector, M-420 data module and Bondapak-C18 column (Rad Pak A in a Z module) as stationary phase. All equipment was from Waters Scientific Co., Mississauga, Ontario. The mobile phase consisted of methanol/0.05M potassium phosphate buffer, pH 4.0. The methanol content of the mobile phase depended upon the particular separation. A short precolumn (packed with Bondapak $C_{18}$/Corasil) was used to guard the main column. UV-absorbing material was detected at 220 nm at a sensitivity of 0.02 AUFS.

EXAMPLE 9

Cyclization and Ring Expansion of Unnatural Peptide Substrates

The procedure of Example 6 was repeated with ACV analogs in which valine was replaced by alpha-aminobutyric acid ($R_1 = R_2 = H$) and allo-isoleucine ($R_1 = H$, $R_2 = C_2H_5$), as follows:
(AC-aminobutyrate)$_2$ (ACAB)$_2$ and (AC-isoleucine)$_2$- (ACI)$_2$ were dissolved in water neutralized and lyophilized in 0.1 and 1.0 mg amounts. These peptides were then used as substrates in cyclization and ring expansion assays as follows: One hundred micrograms of (ACV)$_2$ from Example 6 was used as substrate in a cyclization and a ring expansion assay system using 0.1 ml of salt-precipitated cell-free extract as enzyme source in each case. (Final concentration of (ACV)$_2$ is 0.306 mM). Identical cyclization and ring expansion assays were set up in which 100 μg (ACAB)$_2$ or 1.0 mg (ACI)$_2$ replaced the (ACV)$_2$ as substrate and 0.3 ml of salt precipitated cell-free extract was used as enzyme source. No substrate controls were also prepared. The reaction mixtures were incubated for 2 h at 20° C. At the end of incubation 20 μl amounts of the cyclization reaction mixtures were bioassayed versus *M. luteus* and *E. coli* Ess; 20 μl amounts of the ring expansion reaction mixtures were bioassayed versus *E. coli* Ess plus and minus penicillinase.

The remaining reaction mixtures were then mixed with an equal volume of methanol and centrifuged in preparation for HPLC analysis.

Cyclization and ring expansion reaction mixtures containing (ACI)$_2$ as substrate and also the no substrate controls were analyzed using a mobile phase of 20% Methanol/80% KH$_2$PO$_4$, 0.05M adjusted to pH 4.0 with H$_3$PO$_4$. Twenty microliter amounts were injected and eluted at a flow rate of 2 ml/min.

Cyclization and ring expansion reaction mixtures containing (ACV)$_2$, (ACI)$_2$ and (ACAB)$_2$ as substrates and also the no substrate controls were then analyzed using a mobile phase of 5% Methanol/95% KH$_2$PO$_4$, 0.05M adjusted to pH 4.0 with H$_3$PO$_4$. Twenty microliter amounts were injected and eluted at a flow rate of 2 ml/min for 5 min rising to 3 ml/min by 7 min and remaining at 3 ml/min for the rest of the analysis time.

RESULTS AND DISCUSSION

Results of biological assays of the reaction mixtures are seen in Table 1. Cyclization of (ACV)$_2$ results in formation of a bioactive product. The zone size produced on *E. coli* Ess agar plates (28.0 mm) is equivalent to the zone size which a cephalosporin C solution at 29.3 μg/ml would produce. Cyclization of (ACAB)$_2$ produces a bioactive product with antibiotic activity equivalent to a 0.9 μg/ml solution of cephalosporin C against *E. coli* Ess. Similarly cyclization of (ACI)$_2$ produces a bioactive product with antibiotic activity equivalent to a 4.85 μg/ml solution of cephalosporin C against *E. coli* Ess. Ring expansion assays containing (ACV)$_2$ result in formation of penicillinase-insensitive antibiotic which produces a zone size on *E. coli* Ess+penicillinase plates (22 mm) equivalent to a 7.6 μg/ml solution of cephalosporin C. Ring expansion assays containing (ACAB)$_2$ do not form penicillinase-insensitive antibiotic nor do they form any antibiotic affecting *E. coli* Ess. Since antibiotic activity was seen in (ACAB)$_2$-containing cyclization assay systems, this implies one of two things: 1. The additional components in a ring expansion reaction mixture inhibit cyclization of ACAB, or 2. Ring expansion assays containing (ACAB)$_2$ produce a cephalosporin which does not affect *E. coli* Ess. Ring expansion assays containing (ACI)$_2$ form penicillinase-insensitive antibiotic which produces a zone size on *E. coli* Ess+penicillinase plates (12.5 mm) eqivalent to a 0.9 μg/ml solution of cephalosporin C.

HPLC analysis of cyclization reaction mixtures containing (ACI)$_2$ as substrate was carried out with a mobile phase of 20% methanol/80% KH$_2$PO$_4$, 0.05M pH 4.0. When compared with the no substrate control, (ACI)₂ containing reaction mixtures showed a new peak at 2.66 min. Analysis of ring expansion reaction mixtures under the same conditions did not show any new peak because the region around 2.66 min was obscured by UV absorbing material (α-ketoglutarate), present in both the no substrate control and in the test.

When the mobile phase was changed to 5% Methanol/95% $KH_2PO_4$, 0.05M pH 4.0, cyclization reaction mixtures containing (ACI)₂ now showed the new peak to be at 11.26 min.

Ring expansion reaction mixtures containing (ACI)₂ showed the new peak to be somewhat (~50%) reduced in size with a smaller peak running just in front of the main peak. This is expected since cephalosporins typically run close to, but just in front of, their corresponding penicillin.

Cyclization reaction mixtures containing (ACAB)₂ as substrate showed a new peak in the region of 2.33 min. The corresponding ring expansion reaction mixtures also show their new peak at 2.3 min. Since ring expansion reaction mixtures do no show bioactivity despite the presence of this new peak, we conclude that the cephalosporin is being formed but is of lower antibiotic activity against *E. coli* Ess than the corresponding penicillin. Analysis of (ACV)₂ containing reaction mixtures shows that the natural product formed in cyclization reaction mixtures, a mixture of isopenicillin N and penicillin N [(iso)penicillin N], elutes at a retention time of 5.23 min. Ring expansion results in conversion of some of the penicillin to desacetoxy cephalosporin C which runs with a retention time of 4.76 min and does not separate from (iso)penicillin N under these conditions.

Based on these studies, it is concluded that salt precipitated cell-free extract from *S. clavuligerus*, can cyclize (ACI)₂ and (ACAB)₂ to form penicillins, in addition to being able to cyclize the natural substrate, (ACV)₂. The unnatural penicillins so formed have chromatographic characteristics distinct from (iso)penicillin N and there is no evidence for production of (iso)penicillin N in reaction mixtures containing unnatural peptide substrates. The same enzyme preparation can cause ring expansion of the penicillin formed from (ACI)₂, resulting in formation of a new cephalosporin.

TABLE 1

| Substrate and Assay Conditions | Zone of Inhibition (mm) | | |
|---|---|---|---|
| | *M. luteus* | *E. coli* Ess | *E. coli* Ess + penicillinase |
| (ACV)₂ cyclization | 29.0 | 28.0 | |
| (ACV)₂ ring expansion | | 28.5 | 22.0 |
| (ACAB)₂ cyclization | 8.0 | 12.5 | |
| (ACAB)₂ ring expansion | | 8.0 | 0 |
| (ACI)₂ cyclization | 13.0 | 20.0 | |
| (ACI)₂ ring expansion | | 20.0 | 12.5 |
| no substrate cyclization | ± | ± | ± |
| no substrate ring expansion | ± | ± | ± |

We claim:

1. A process for isolating cyclase, epimerase and a ring expansion enzyme from a cell-free extract of a prokaryotic beta-lactam producing organism comprising:
    (a) precipitating contaminating proteins from said cell-free extract by addition of ammonium sulfate to 40% saturation;
    (b) separating precipitated protein from a supernatant;
    (c) adding ammonium sulfate to 70% saturation to said supernatant thereby precipitating desired enzymes;
    (d) suspending said precipitated desired enzymes in pH 7 buffer;
    (e) separating the epimerase by gel filtration chromatography; and
    (f) separating the cyclase and ring expansion enzymes from each other by ion exchange chromatography.

2. A process as claimed in claim 1 wherein said prokaryotic organism is selected from the group comprising *S. clavuligerus*, *S. cattleya* and *S. lipmanii*.

3. A process as claimed in claim 2 wherein said prokaryotic organism is *S. clavuligerus*.

* * * * *